(12) United States Patent
Guo et al.

(10) Patent No.: US 11,873,509 B2
(45) Date of Patent: Jan. 16, 2024

(54) METHOD FOR CONTINUOUS CULTURE OF SHRIMP CELLS

(71) Applicant: Ocean University of China, Qingdao (CN)

(72) Inventors: Huarong Guo, Qingdao (CN); Xin Song, Qingdao (CN); Yang Zhou, Qingdao (CN)

(73) Assignee: Ocean University of China, Qingdao (CN)

( * ) Notice: Subject to any disclaimer, the term of this patent is extended or adjusted under 35 U.S.C. 154(b) by 692 days.

(21) Appl. No.: 16/860,315

(22) Filed: Apr. 28, 2020

(65) Prior Publication Data
US 2021/0009943 A1 Jan. 14, 2021

(30) Foreign Application Priority Data
Jul. 10, 2019 (CN) .......................... 201910622127.X

(51) Int. Cl.
*C12N 5/07* (2010.01)

(52) U.S. Cl.
CPC ........ *C12N 5/0601* (2013.01); *C12N 2500/30* (2013.01); *C12N 2500/32* (2013.01); *C12N 2500/34* (2013.01); *C12N 2500/60* (2013.01); *C12N 2500/82* (2013.01); *C12N 2501/11* (2013.01); *C12N 2501/115* (2013.01); *C12N 2513/00* (2013.01)

(58) Field of Classification Search
CPC .............. C12N 5/0601; C12N 2500/30; C12N 2500/32; C12N 2513/00
See application file for complete search history.

(56) References Cited

FOREIGN PATENT DOCUMENTS

| CN | 103232969 A1 * | 8/2013 | ............... C12N 5/07 |
| CN | 105754928 A1 * | 7/2017 | ............... C12N 5/07 |

OTHER PUBLICATIONS

Corning, Extraction of Three-Dimensional Structures from Corning Matrigel Matrix, Guidelines for Use. (Year: 2019).*
Rubio et al., Cell-Based Fish: A Novel Approach to Seafood Production and an Opportunity for Cellular Agriculture, Frontiers in Sustainable Food Systems, 3(43): 1-13. (Year: 2019).*
Corning, Corning Matrigel Basement Membrane Matrix for 3D Culture In Vitro, Protocol. (Year: 2017).*
HPW Lab, Gastrointestinal Stem Cell Culture protocol, MD Anderson Cancer Center. (Year: 2014).*
Shimizu et al., Hemolymph analysis and evaluation of newly formed media for culture of shrimp (*Penaeus stylirostris*), In Vitro Cell Dev Biol, 37: 322-329. (Year: 2001).*
Chazotte, Labeling Golgi with Fluorescent Ceramides, Cold Spring Harbor Laboratory Press, p. 913-915. (Year: 2012).*
Chen et al., Establishment of cell culture systems from penaeid shrimp and their susceptibility to white spot disease and yellow head viruses, Methods in Cell Science, 21: 199-206. (Year: 1999).*
Kumar et al., Development of a cell culture system from the ovarian tissue of African catfish (*Clarias gariepinus*), Acquaculture, 194: 51-62. (Year: 2001).*
Guo et al., CN103232969A1, machine translation by Clarivate Analytics. (Year: 2013).*
Guo et al., CN105754928A1, machine translation by Clarivate Analytics. (Year: 2016).*
Millamena et al., Quantitative dietary requirements of postlarval tiger shrimp, Penaeus monodon, for histidine, isoleucine, leucine, phenylalanine and tryptophan, Aquaculture, 179: 169-179. (Year: 1999).*
RMBIO, Phosphate-Buffered Saline (PBS), retrieved from internet Oct. 30, 2023. (Year: 2023).*
Dang et al., Design and evaluation of a highly porous thermosensitive hydrogel with low gelation temperature as a 3D culture system for Penaeus chinensis lymphoid cells, Carbohydrate Polymers, 88: 361-368. (Year: 2012).*

* cited by examiner

*Primary Examiner* — Laura Schuberg
*Assistant Examiner* — Joseph Paul Miano
(74) *Attorney, Agent, or Firm* — Troutman Pepper Hamilton Sanders LLP; Christopher C. Close, Jr.

(57) ABSTRACT

By establishing effective methods for shrimp 3D cell culture and passage, the present invention provides a technology of continuous shrimp cell culture intended for the establishment of immortalized shrimp cell lines. The present invention provides a preparation method of matrigel for 3D cell culture of shrimp by optimizing an additive proportion of matrigel. The present invention further provides a technology of separation and 3D cell culture of shrimp haemolymph cells, where shrimp haemolymph cells adhere to and grow on the surface of the matrigel in the form of a single round cell and a cell pellet/cellular spheroid, with survival and growth abilities being superior to 2D culture effects. The above technology is achieved by optimizing a formula of complete medium for shrimp cells, selecting the medium as an anticoagulant and a diluent for shrimp haemolymph cells, selecting a 3D culture method for surface-adhered growth in the matrigel.

12 Claims, 5 Drawing Sheets

METHOD FOR CONTINUOUS CULTURE OF SHRIMP CELLS

CROSS REFERENCE TO RELATED APPLICATIONS

This application claims priority, and benefit under 35 U.S.C. § 119(a) of Chinese Patent Application No. 201910622127.X filed 10 Jul. 2019 The disclosure of the prior application is hereby incorporated by reference as if fully set forth below.

TECHNICAL FIELD

The present invention relates to the technical field of animal cell and tissue culture, and in particular to a method for a continuous culture of shrimp cells.

BACKGROUND

Frequent outbreak of shrimp viral diseases has seriously affected shrimp aquaculture, and becomes a bottleneck of sustainable development of shrimp aquaculture. Establishment of immortalized shrimp cell lines can provide an effective research means and a support for the isolation and purification of shrimp viruses, research on pathogenesis, and production of efficient antiviral vaccines. Experts and scholars in China and overseas have made lots of efforts on the establishment of shrimp cell lines. However, all the attempts on the establishment of immortalized shrimp cell lines have failed because shrimp cells hardly divide in culture systems established so far, and are extremely sensitive to various proteases including trypsin and thus very hard to be passaged.

So far, various attempts to culture shrimps in vivo have been made based on two-dimensional (2D) cultures, i.e., cells seeded in culture flasks, Petri dishes, and culture plates grow and survive in a cell monolayer manner. Nowadays, facing the present situation that shrimp 2D cell culture has difficulty in taking a step, it is necessary to make an attempt at shrimp 3D cell culture in order to increase the in vitro growth and survival abilities of shrimp cells. Moreover, because 3D cultured cells do not grow in an adherent manner, various digestive enzymes, including trypsin, may not be used for cell passage, so as to reduce protease's harm to shrimp cells during passage and make continuous shrimp cell culture in vitro possible. However, current efforts on 3D culture and passage of shrimp cells are poor.

SUMMARY

An objective of the present invention is to provide a method for a continuous culture of shrimp cells and use the method to establish an immortalized shrimp cell line, so as to cover the shortage of the prior art.

The present invention firstly provides a method for shrimp 3D cell culture, where the culture method is performed by adding a shrimp cell suspension to culture wells with matrigel, replenishing a complete medium for shrimp cells, culturing in a $CO_2$ incubator, and changing the complete medium for shrimp cells in the culture period;

Where the culture wells with matrigel are prepared by adding the matrigel precooled at 4° C. into culture wells at a proportion of 55 to 80 µL/cm², spreading out and solidifying the matrigel.

The shrimp cells are derived from the circulating haemolymph of shrimps.

The complete medium for shrimp cells is a shrimp cell basal medium supplemented with 15% fetal bovine serum, 20% shrimp ovarian extract, 20 µg/L basic fibroblast growth factor (bFGF) and 20 µg/L epidermal growth factor (EGF) before use.

A formulation of the shrimp cell basal medium includes: 20.55 g/L Leibovitz's L-15 medium (powder), 5 g/L NaCl, 2 g/L glucose, 1 g/L $NaHCO_3$, 166.7 mg/L histidine, 50 mg/L lysine, 50 mg/L methionine, 33.3 mg/L tryptophan, 30 mg/L proline, 30 mg/L taurine, 0.25 mg/L amphotericin B, 100 IU/L penicillin, and 100 mg/L streptomycin, at a pH of 7.2 to 7.4.

The ovarian extract is extracted at 4° C. by the foregoing shrimp cell basal medium after homogenizing shrimp ovarian tissues, and the extract is centrifuged for supernatant at 4° C. at 10,000 rpm; the supernatant is prepared by suction filtration sterilization using 0.45 and 0.22 um filter membranes successively.

The culture is performed in a 3% $CO_2$ incubator at 28° C.

The present invention further provides a method for passage of 3D cultured shrimp cells, where the method for passage includes steps of: washing the shrimp cells cultured on the surface of the matrigel with PBS pre-cooled at 0 to 4° C., adding a cell recovery solution with the same osmotic pressure as the complete medium for shrimp cells, and subsequently dissolving the matrigel at 0 to 4° C.; centrifuging the dissolved matrigel-cell suspension for 5 to 10 min at 3,000×g at 4° C., and discarding supernatant; re-suspending pellets with the complete medium for shrimp cells, and seeding in the matrigel of a new culture plate for passage.

A formulation of the PBS is as follows: 12.0 g/L NaCl, 0.3 g/L KCl, 4.5 g/L $Na_2HPO_4 \cdot 12H_2O$, and 0.3 g/L $KH_2PO_4$, at a pH of 7.2 to 7.4, autoclaved, and stored at 4° C.

An osmotic pressure of the cell recovery solution is 560 to 620 mOsm/kg.

The matrigel prepared by the present invention can effectively promote the aggregation and pelletization of shrimp cells to achieve stereoscopic growth. Shrimp cells have significantly higher optimal osmotic pressure than mammalian cells. Thus, the present invention uses a complete medium for shrimp cells as an anticoagulant and a diluent, and uses an osmotic pressure heightening the PBS for cell washing and the cell recovery solution, effectively avoiding hypotonic rupture of the shrimp haemolymph cells during extraction and passage and increasing the separation and recovery efficiency of shrimp haemolymph cells. A measure for timely medium change 4 h after seeding relieves a blackening progress of the medium and reduces the toxicity of the blackening to shrimp haemolymph cells. Shrimp haemolymph cells are significantly smaller than mammalian cells. Thus, use of higher centrifugal velocity ensures full precipitation and recovery of shrimp haemolymph cells. Dissolution process of the matrigel in the cell recovery solution does not involve proteinase digestion, avoiding a harmful effect of enzymatic digestion and passage on shrimp cells; 3D cultured shrimp cells grow stereoscopically in the form of non-spread single round cell or cellular spheroid, which is conducive to cell survival and division in vitro.

DETAILED DESCRIPTION

Figure 1A:
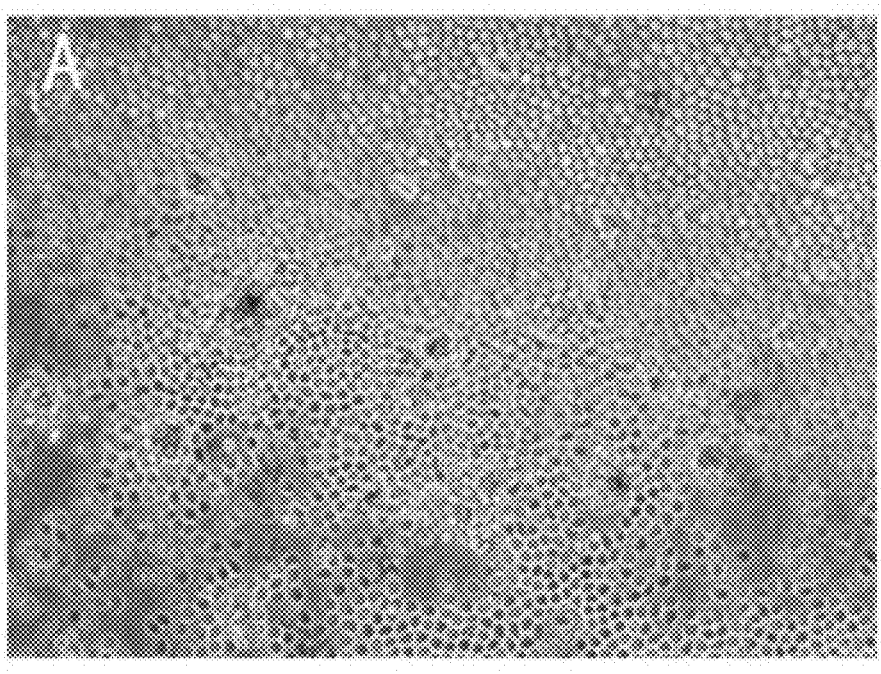
FIGS. 1A-1D show micrographs of results of 3D culture of shrimp haemolymph cells, where Panels A, B, C, and D are optical micrographs of cells seeded on the surface of a matrigel for 6 h, and 1, 4 and 5 days, respectively.
Figure 1B:
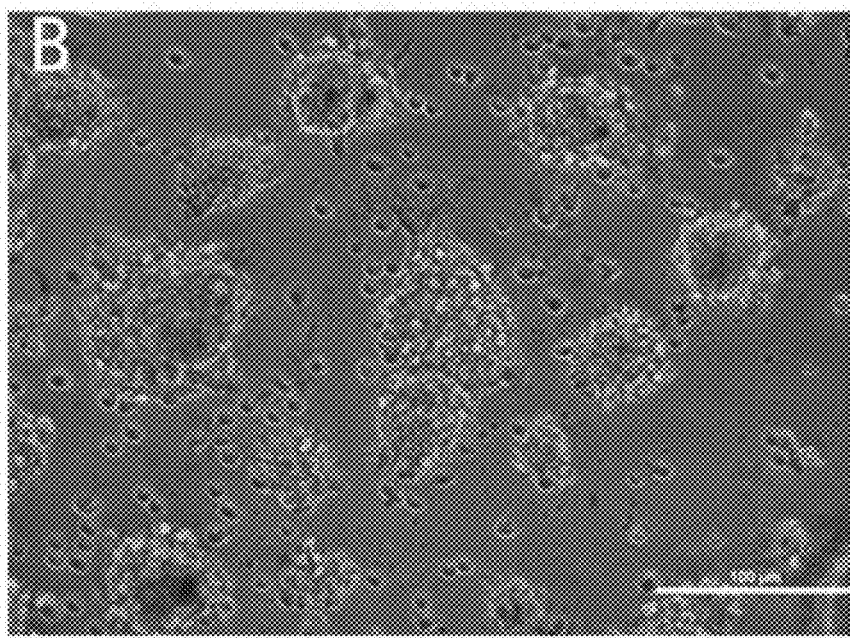
Figure 1C:
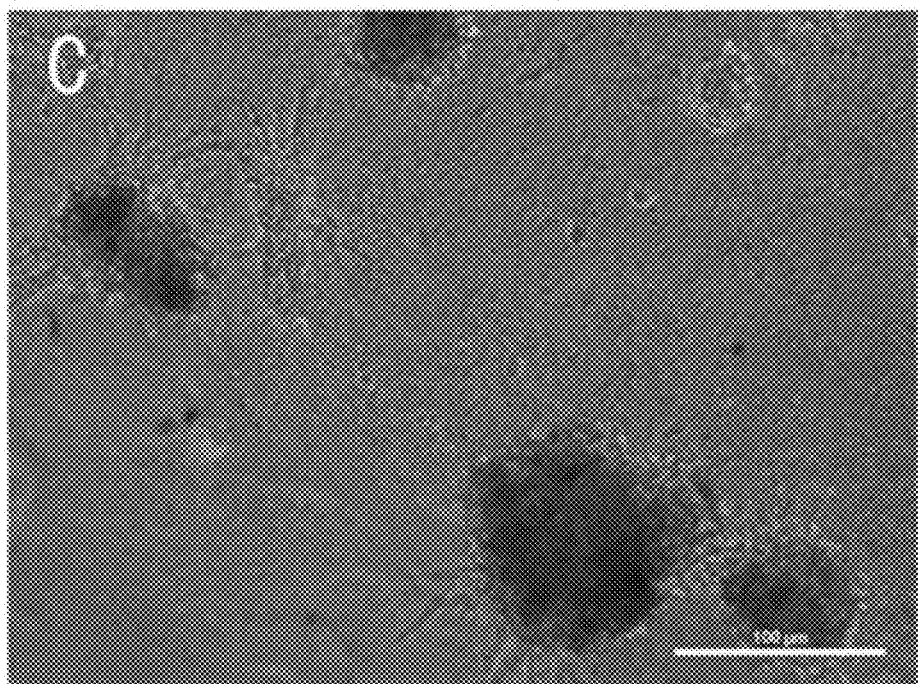
Figure 1D:
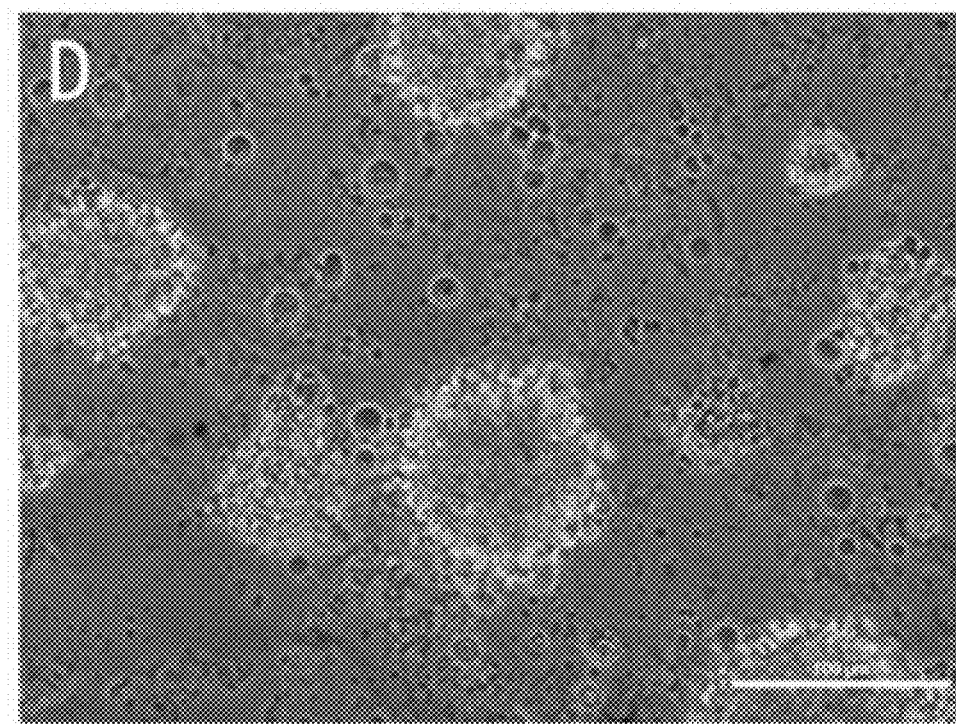

It was found during shrimp cell culture that: when shrimp cells were seeded on the surface of a matrigel, the growth and survival abilities of the in vitro cultured shrimp cells were improved significantly, and large cell pellets were formed on the surface of the matrigel; however, embedding shrimp cells in the matrigel was less effective than seeding on the surface of the matrigel. However, sodium alginate was poorly effective in use in shrimp 3D cell culture, which was easy to pollute; a shrimp cell was present in the form of a single round cell, which did not form a cellular spheroid and could not survive and grow well. Moreover, applicants found that shrimp haemolymph cells had higher osmotic pressure than mammalian cells. If common normal saline or phosphate buffer solution (PBS) is used as an anticoagulant and a diluent, shrimp haemolymph cells will lyse rapidly due to low permeability. Therefore, the present invention uses a complete medium for shrimp cells or a PBS heightening the osmotic pressure as an anticoagulant and a diluent for shrimp haemolymph cells.

It is on the basis of the above finding that the present invention establishes and optimizes methods for shrimp 3D cell culture and passage, and further provides a technology of continuous shrimp cell culture, laying the foundation for the establishment of immortalized shrimp cell lines.

To better explain the present invention, examples of 3D culture and passage of shrimp haemolymph cells will further describe the main point of the invention:

Embodiment 1: Preparation of Matrigel for Shrimp 3D Cell Culture

Matrigel product used is Corning® Matrigel® Basement Membrane Matrix Phenol Red Free (Cat. NO. 356237).

Specific steps are as follows:
(1) Thawing of matrigel. Centrifuge tubes with matrigel were stored on an ice bath overnight in a refrigerator at 4° C., and shaken well after thawing.
(2) Plating of matrigel. A culture plate and a vaccinator tip were pre-cooled on ice, and the matrigel was added into the culture plate at a proportion of 55 to 80 µl/cm².
(3) After the matrigel was spread out spontaneously, the culture plate was solidified in an incubator for 30 min at 37° C. for use.

The above-mentioned proportion of matrigel addition was a repeatedly optimized result. After spreading out spontaneously, the matrigel added did not fill up the bottom of the whole culture well fully, but a gap was still left between the matrigel and the side wall of the culture well. Nevertheless, a matrigel platform large enough to support shrimp 3D cell culture could be formed in the center of the culture well.

Embodiment 2: Isolation and 3D Culture of Shrimp Haemolymph Cells

Isolation and 3D culture of shrimp haemolymph cells included the following steps:

(1) processing a shrimp in boiling disinfected seawater supplemented with 1,000 IU/mL penicillin and 1,000 µg/mL streptomycin for 12 to 24 h;
(2) before extracting haemolymph, immersing and disinfecting a shrimp in 75% ethanol for 3 to 5 min to achieve anesthesia;
(3) scrubbing a sampling site, i.e., thoracic sinus of the hypogastrium of the shrimp, with an iodophor cotton ball and a 75% alcohol wipe successively;
(4) withdrawing approximately 0.2 to 0.5 mL of complete medium for shrimp cells into a 1-mL syringe, drawing shrimp haemolymph from the thoracic sinus of the hypogastrium of the shrimp, and mixing well immediately;
(5) after drawing haemolymph, removing a syringe needle, and injecting the haemolymph suspension in the syringe into culture wells with matrigel prepared in Embodiment 1 slowly;
(6) replenishing the complete medium for shrimp cells, and culturing in a 3% $CO_2$ incubator at 28° C.;
(7) changing the medium 4 h after shrimp haemolymph cells adhered to the wall; and (8) afterwards, changing the medium in time approximately once or twice a day according to color changes of the complete medium for shrimp cells (i.e., yellow discoloration).

A method for preparing the foregoing boiling disinfected seawater included the steps of: filtering natural seawater through gauze and filter paper, boiling and disinfecting for 5 min, cooling down, and adding 1,000 IU/mL penicillin and 1,000 µg/mL streptomycin.

A method for preparing the complete medium for shrimp cells included the following steps:
(1) Preparation of shrimp cell basal medium: dissolving 20.55 g of Leibovitz's L-15 medium (powder), 5 g of NaCl, 2 g of glucose, 1 g of $NaHCO_3$, 166.7 mg of histidine, 50 mg of lysine, 50 mg of methionine, 33.3 mg of tryptophan, 30 mg of proline, 30 mg of taurine, 0.25 mg of amphotericin B, $1.0 \times 10^5$ IU penicillin, and 100 mg of streptomycin in 1 L of ultrapure water, adjusting pH to 7.2 to 7.4, conducting filtration sterilization through a 0.22 µm microporous membrane, dispensing, and storing at −20° C.; and
(2) Preparation of a complete medium for shrimp cells: adding 15% fetal bovine serum, 20% shrimp ovarian extract, 20 µg/L basic fibroblast growth factor (bFGF) and 20 µg/L epidermal growth factor (EGF) in the shrimp cell basal medium before use.

A method for preparing the ovarian extract included steps of: mincing shrimp ovarian tissues into a 50-mL centrifuge tube; grinding the tissues thoroughly with a tissue homogenizer; adding the pre-cooled complete medium for shrimp cells into ovarian tissue homogenate at a proportion of 20 mL per gram of tissue, and storing in a refrigerator overnight at 4° C.; centrifuging for 15 min for supernatant at 4° C. at 10,000 rpm; centrifuging for 30 min for supernatant at 4° C. at 10,000 rpm; conducting suction filtration sterilization using 0.45 and 0.22 um filter membranes successively, dispensing, and storing at −20° C.

Figure 2A:
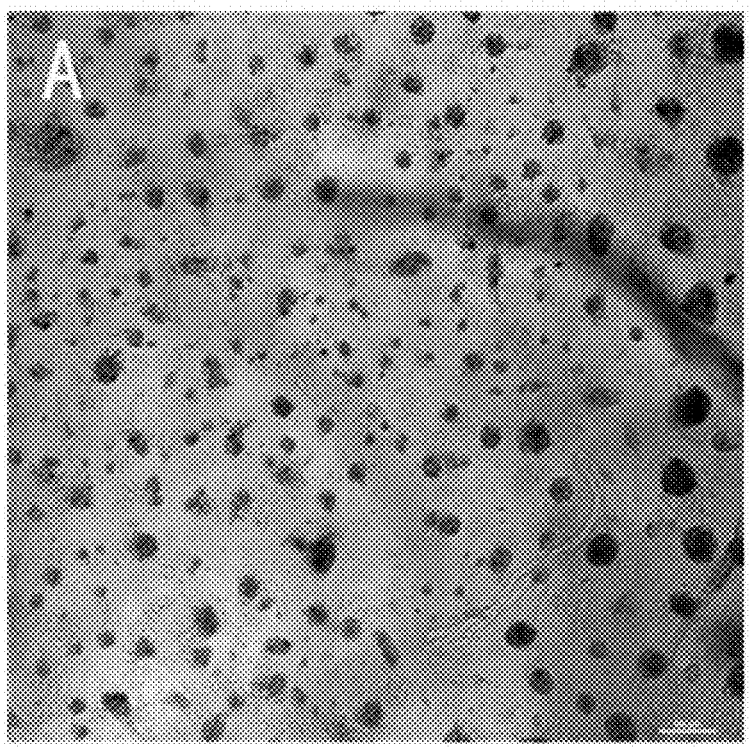
FIGS. 2A-2C show results of Calcein AM staining 9 days after 3D culture of shrimp haemolymph cells. Panels A, B, and C represent an optical micrograph (A), a fluogram (B), and a photomerger (C) of cells under confocal fluorescence microscope, respectively.
Figure 2B:
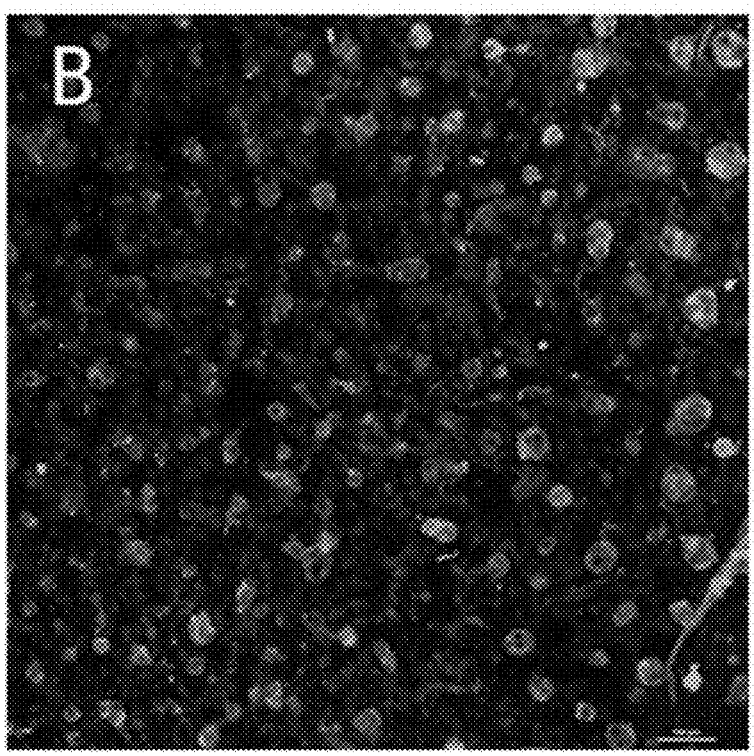
Figure 2C:
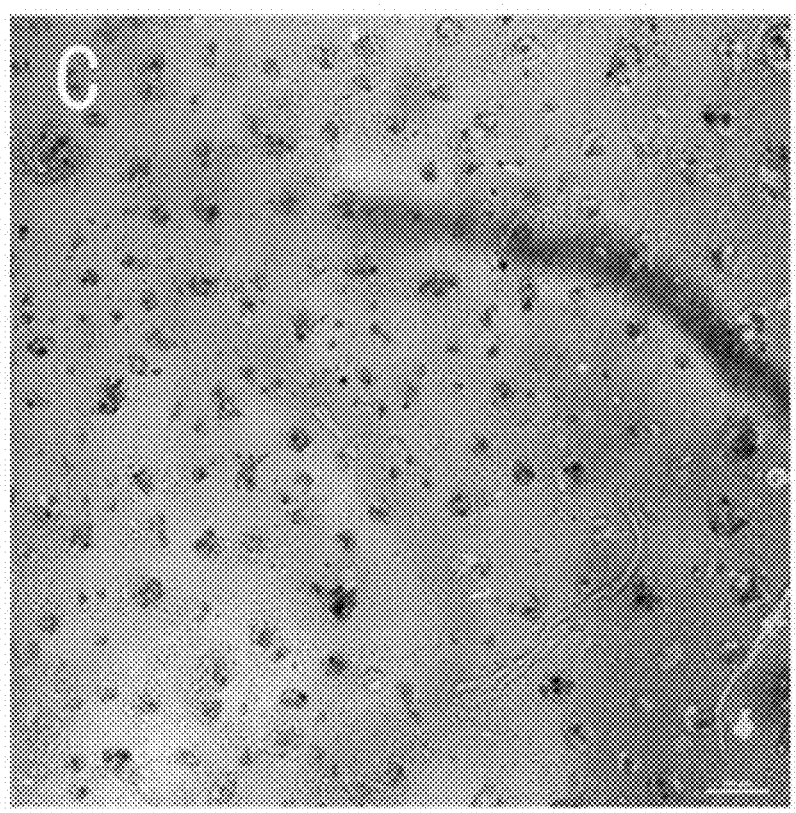

Culture results are shown in FIGS. 1A-1D. Shrimp haemolymph cells adhere to the surface of the matrigel and grow stereoscopically in the form of a single round cell and a cell pellet/cellular spheroid, and aggregate into cell pellets/cellular spheroids measuring 50 to 110 um one day later. Results of dyeing with cytoactive fluorescent dye Calcein-AM are shown in FIGS. 2A-2C. Viable cells are present on the surface and internal of cell pellets/cellular spheroids 9 days after 3D culture, and strong green fluorescent signals can be observed. Visibly, survival and growth abilities of 3D cultured shrimp haemolymph cells are superior to those achieved by 2D culture.

Embodiment 3: Passage of 3D Cultured Shrimp Cells

Taking passage of shrimp haemolymph cells seeded and grown on the surface of the matrigel for example, detailed steps were as follows:
(1) washing cells once with PBS pre-cooled on ice;
(2) adding a modified cell recovery solution (Corning, Cat. NO. 354253) at a proportion of 2 mL per Petri dish (φ 35 mm); placing the Petri dish on ice, and shaking from side to side until the matrigel was dissolved;
(3) collecting the dissolved matrigel-cell suspension in a 1.5 mL centrifuge tube, centrifuging for 5 to 10 min at 3,000×g at 4° C., and discarding supernatant; and
(4) re-suspending cell pellets with the complete medium for shrimp cells, seeding on the matrigel of a new culture plate, and conducting static culture in a 3% $CO_2$ incubator at 28° C.

A method for preparing the PBS included the steps of: separately weighing and dissolving 12.0 g of NaCl, 0.3 g of KCl, 4.5 g of $Na_2HPO_4 \cdot 12H_2O$, and 0.3 g of $KH_2PO_4$ in 1 L of pure water, adjusting pH to 7.2 to 7.4 with 3M NaOH, autoclaving, dispensing, and storing at 4° C. for use.

A method for preparing the modified cell recovery solution included the steps of: adding 20 mg/mL NaCl in cell recovery solution (Corning, Cat. NO. 354253), heightening an osmotic pressure to 560 to 620 mOsm/kg.

Figure 3A:
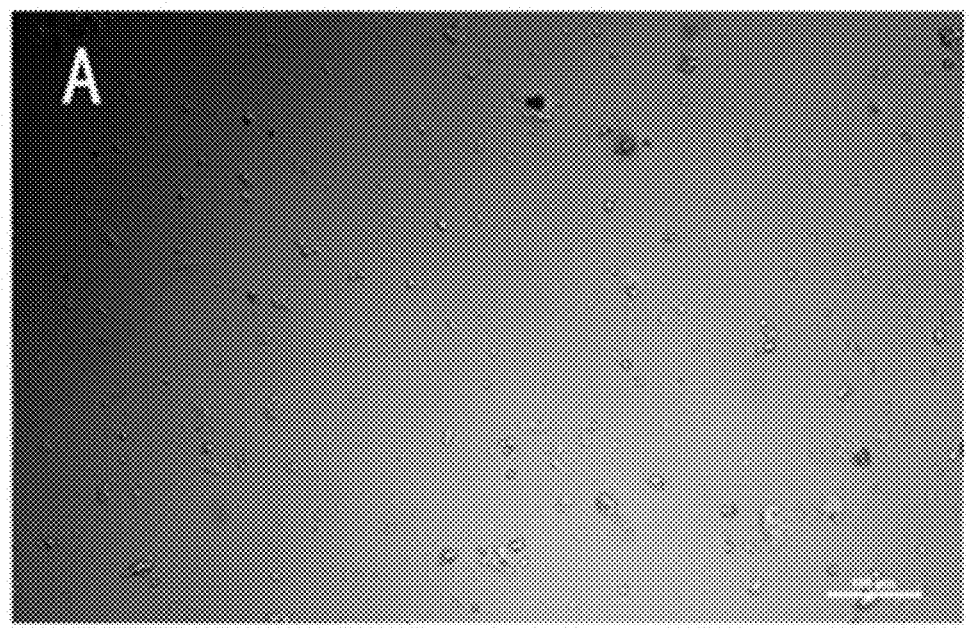
FIGS. 3A-3C show results of Calcein AM staining 3 days after passage of 3D cultured shrimp haemolymph cells. Panels A, B, and C represent an optical micrograph (A), a fluogram (B), and a photomerger (C) of cells under confocal fluorescence microscope, respectively.
Figure 3B:
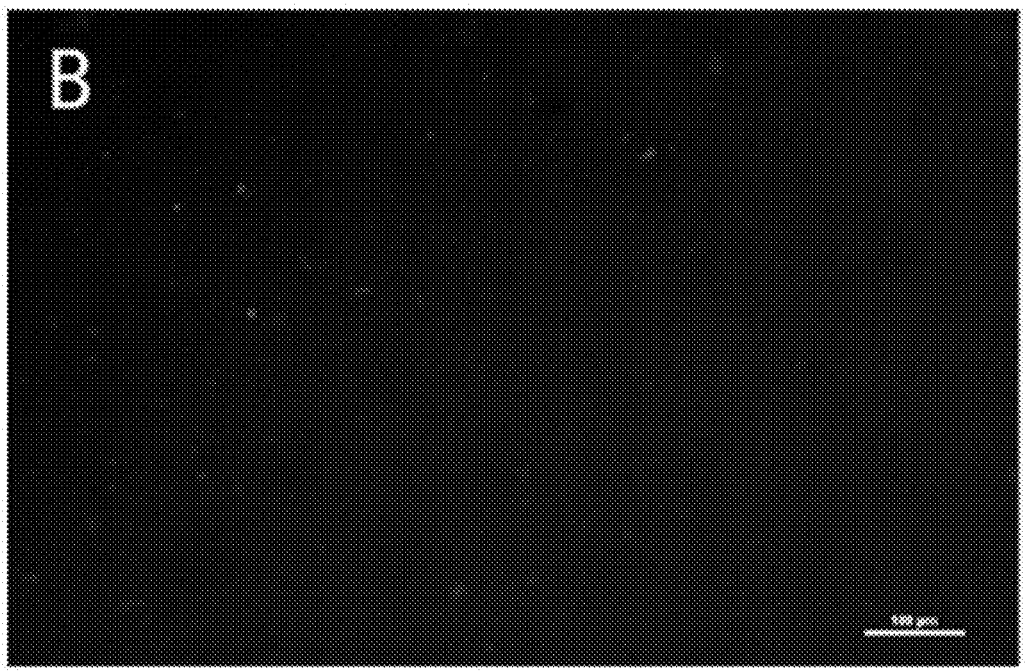
Figure 3C:
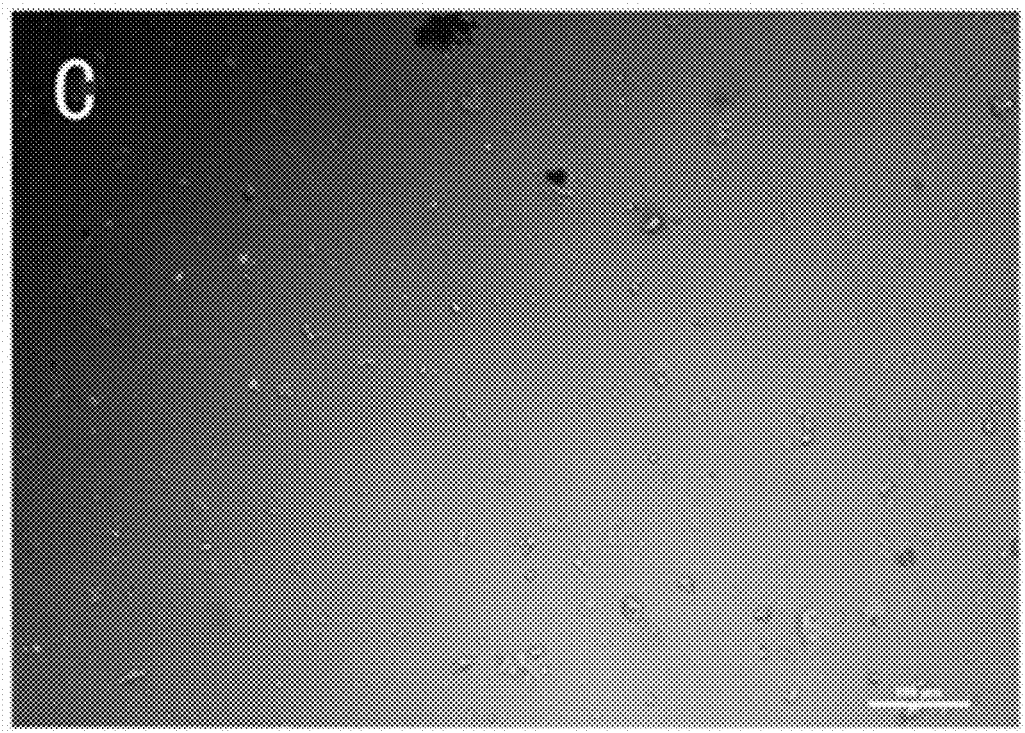

As shown in FIGS. 3A-3C, the shrimp haemolymph cells passaged can adhere to and grow on the surface of the Matrigel better, and survival rate can be as high as more than 90% after passage.

The methods of the present invention are further suitable for cells derived from other shrimp tissues.

What is claimed is:

1. A method for passage of three-dimensional (3D) cultured shrimp cells, wherein the method for passage comprises steps of: 3D culturing shrimp cells, washing the 3D cultured shrimp cells with phosphate-buffered saline (PBS) pre-cooled at 4° C., adding a cell recovery solution with an osmotic pressure that is the same as a complete medium for shrimp cells, and subsequently dissolving an Engelbreth-Holm-Swarm mouse sarcoma matrix at 0 to 4° C.; centrifuging the dissolved Engelbreth-Holm-Swarm mouse sarcoma matrix cell suspension for 5 to 10 min at 3,000×g at VC, and discarding supernatant; re-suspending pellets with the complete medium for shrimp cells, and seeding on the Engelbreth-Holm-Swarm mouse sarcoma matrix of a new culture plate for passage;
wherein the step of 3D culturing shrimp cells is performed by adding a shrimp cell suspension to culture wells with Engelbreth-Holm-Swarm mouse sarcoma matrix, replenishing the complete medium for shrimp cells, culturing in a $CO_2$ incubator, and changing the complete medium for shrimp cells in a culture period;
wherein the culture wells with Engelbreth-Holm-Swarm mouse sarcoma matrix are prepared by adding the Engelbreth-Holm-Swarm mouse sarcoma matrix pre-cooled at 4° C. into culture wells at a proportion of 55 to 80 μL/cm², spreading out and solidifying the Engelbreth-Holm-Swarm mouse sarcoma matrix;
the complete medium for shrimp cells is a shrimp cell basal medium supplemented with 15% fetal bovine serum, 20% shrimp ovarian extract, 20 μg/L basic fibroblastic growth factor (bFGF) and 20 μg/L epidermal growth factor (EGF) before use; a formulation of the shrimp cell basal medium comprises: 20.55 g/L Leibovitz's L-15 medium powder, 5 g/L NaCl, 2 g/L glucose, 1 g/L $NaHCO_3$, 166.7 mg/L histidine, 50 mg/L lysine, 50 mg/L methionine, 33.3 mg/L tryptophan, 30 mg/L proline, 30 mg/L taurine, 0.25 mg/L amphotericin B, 100 IU/L penicillin, and 100 mg/L streptomycin, at a pH of 7.2 to 7.4.

2. The method for passage according to claim 1, wherein a formulation of the PBS is as follows: 12.0 g/L NaCl, 0.3 g/L KCl, 4.5 g/L $Na_2HPO_4 \cdot 12H_2O$, and 0.3 g/L $KH_2PO_4$, at a pH of 7.2 to 7.4, autoclaved, and stored at 4° C.

3. The method for passage according to claim 1, wherein an osmotic pressure of the cell recovery solution is 560 to 620 mOsm/kg.

4. The method for passage according to claim 1, wherein the shrimp cells are shrimp haemolymph cells.

5. The method for passage according to claim 4, wherein a formulation of the PBS is as follows: 12.0 g/L NaCl, 0.3 g/L KCl, 4.5 g/L $Na_2HPO_4 \cdot 12H_2O$, and 0.3 g/L $KH_2PO_4$, at a pH of 7.2 to 7.4, autoclaved, and stored at 4° C.

6. The method for passage according to claim 4, wherein an osmotic pressure of the cell recovery solution is 560 to 620 mOsm/kg.

7. The method for passage according to claim 1, wherein the ovarian extract is extracted at 4° C. by the foregoing shrimp cell basal medium after homogenizing shrimp ovarian tissues, and the extract is centrifuged for supernatant at 4° C. at 10,000 rpm; the supernatant is prepared by suction filtration sterilization using 0.45 and 0.22 um filter membranes successively.

8. The method for passage according to claim 7, wherein a formulation of the PBS is as follows: 12.0 g/L NaCl, 0.3 g/L KCl, 4.5 g/L $Na_2HPO_4 \cdot 12H_2O$, and 0.3 g/L $KH_2PO_4$, at a pH of 7.2 to 7.4, autoclaved, and stored at 4° C.

9. The method for passage according to claim 7, wherein an osmotic pressure of the cell recovery solution is 560 to 620 mOsm/kg.

10. The method for passage according to claim 1, wherein the culture is performed in a 3% $CO_2$ incubator at 28° C.

11. The method for passage according to claim 10, wherein a formulation of the PBS is as follows: 12.0 g/L NaCl, 0.3 g/L KCl, 4.5 g/L $Na_2HPO_4 \cdot 12H_2O$, and 0.3 g/L $KH_2PO_4$, at a pH of 7.2 to 7.4, autoclaved, and stored at 4° C.

12. The method for passage according to claim 10, wherein an osmotic pressure of the cell recovery solution is 560 to 620 mOsm/kg.

* * * * *